(12) United States Patent
Makley

(10) Patent No.: US 9,480,307 B2
(45) Date of Patent: Nov. 1, 2016

(54) DELAYED RELEASE RESTRAINT SYSTEM

(71) Applicant: University of Maryland, Baltimore, Baltimore, MD (US)

(72) Inventor: Michael Makley, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 708 days.

(21) Appl. No.: 13/803,167

(22) Filed: Mar. 14, 2013

(65) Prior Publication Data

US 2013/0261800 A1 Oct. 3, 2013

Related U.S. Application Data

(60) Provisional application No. 61/616,595, filed on Mar. 28, 2012.

(51) Int. Cl.
| | |
|---|---|
| *G01M 1/38* | (2006.01) |
| *G05B 13/00* | (2006.01) |
| *G05B 15/00* | (2006.01) |
| *G05D 23/00* | (2006.01) |
| *A44B 1/04* | (2006.01) |
| *A44B 11/25* | (2006.01) |
| *A44B 17/00* | (2006.01) |
| *B61D 3/18* | (2006.01) |
| *G08B 21/00* | (2006.01) |
| *A44B 11/00* | (2006.01) |
| *A61F 5/37* | (2006.01) |

(52) U.S. Cl.
CPC ........... *A44B 11/005* (2013.01); *A61F 5/3776* (2013.01); *Y10T 24/2194* (2015.01)

(58) Field of Classification Search
CPC ...... E05B 43/00; E05B 75/00; G09F 3/0329; A61G 3/0808; A61G 13/124; A61G 13/101; A61B 19/00; H01H 71/123; H02B 11/26
USPC ......... 602/20, 21; 361/115, 642, 729; 410/7, 410/23; 340/668, 573
See application file for complete search history.

(56) References Cited

U.S. PATENT DOCUMENTS

| 4,189,022 A | * | 2/1980 | Lazich et al. ................ 180/268 |
| 2005/0083207 A1 | * | 4/2005 | Smith et al. ................ 340/668 |
| 2006/0110230 A1 | * | 5/2006 | Girardin ........................ 410/7 |
| 2009/0211316 A1 | * | 8/2009 | Butler et al. .................. 70/16 |
| 2010/0101060 A1 | * | 4/2010 | Walega et al. ................ 24/603 |

OTHER PUBLICATIONS

"Swedish Belt: Application Instructions", "www.posey.com", 2009, pp. 12, Publisher: Posey Company, Published in: Arcadia, California.

* cited by examiner

*Primary Examiner* — Mohammad Ali
*Assistant Examiner* — Md Azad
(74) *Attorney, Agent, or Firm* — Eugene J. Molinelli; Beusse Wolter Sanks & Maire

(57) ABSTRACT

A restraint method, apparatus and system includes one or more of a restraining strap, a latch and an opening apparatus. The restraining strap is configured to bind a subject to a support structure. The latch is configured to removably engage at least one of two ends of the restraining strap. The opening apparatus includes a first module configured to cause the latch to open, an actuator, and a second module. The second module is configured to cause the first module to open the latch in response to operation of the actuator after a delay of time past the operation of the actuator. The opening module is arranged so that the subject can operate the actuator.

13 Claims, 10 Drawing Sheets

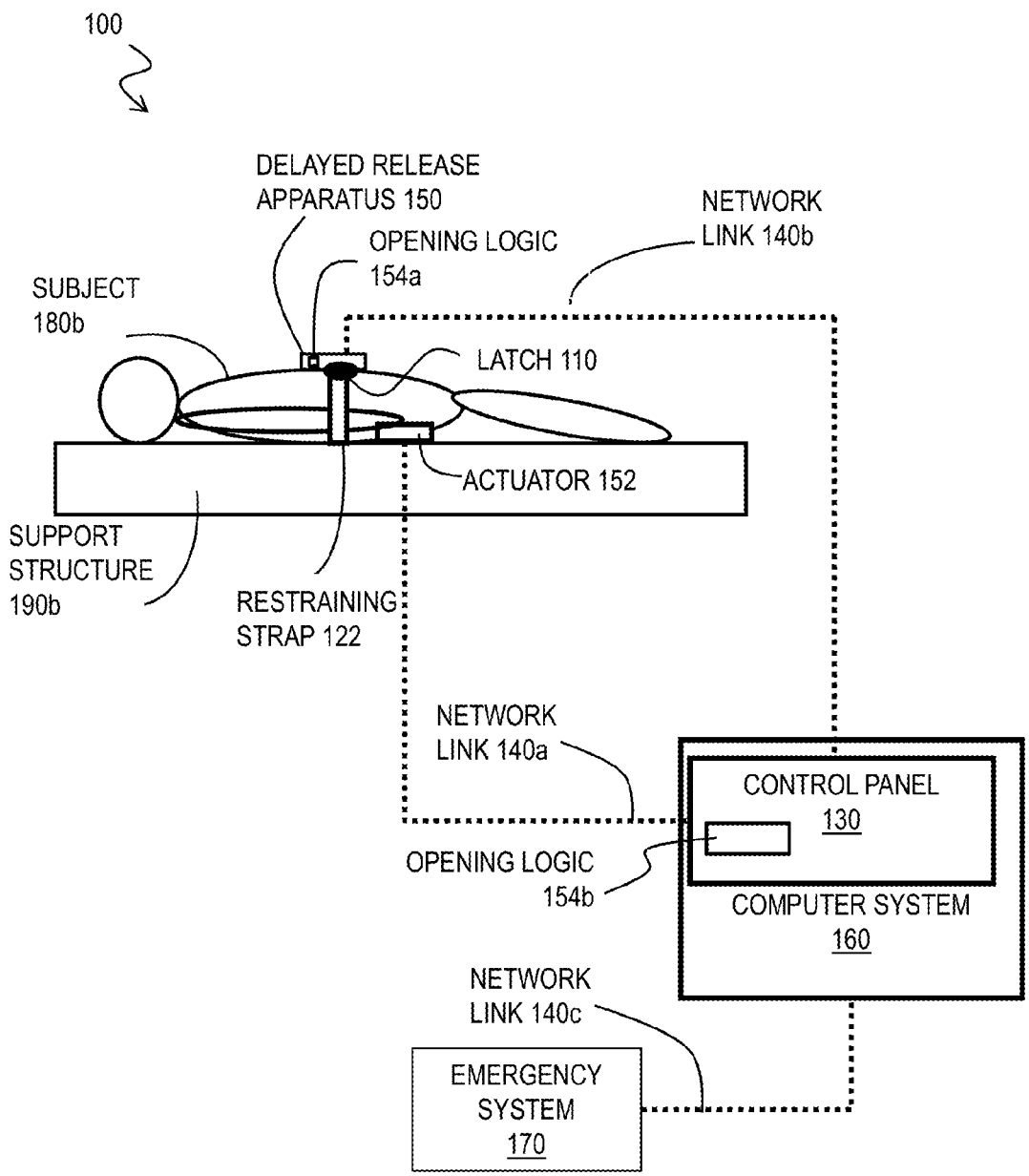

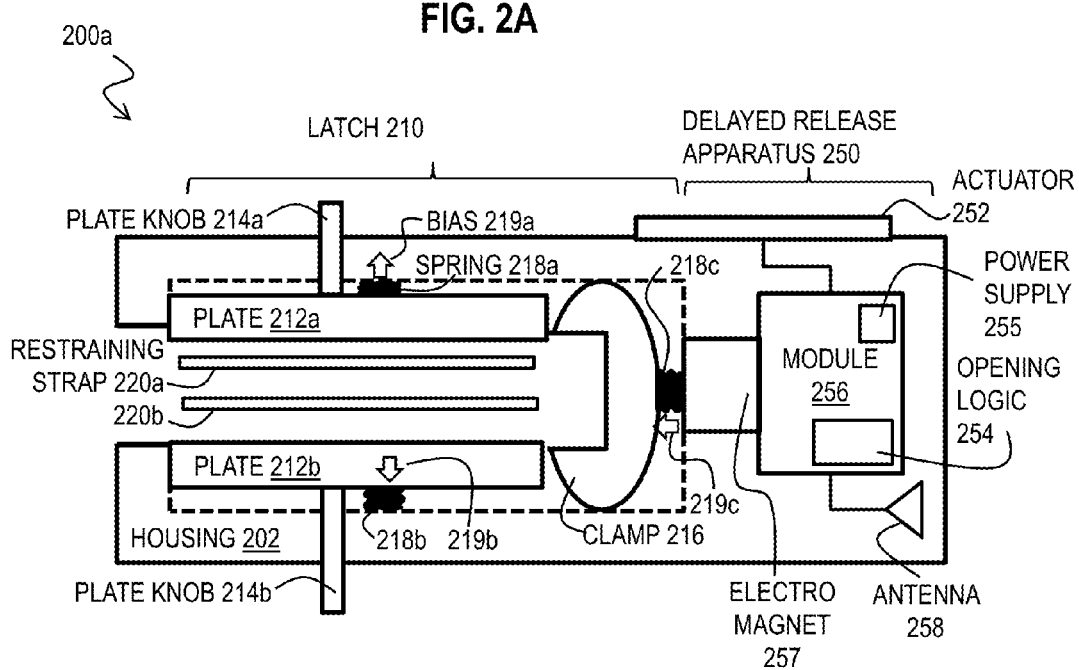
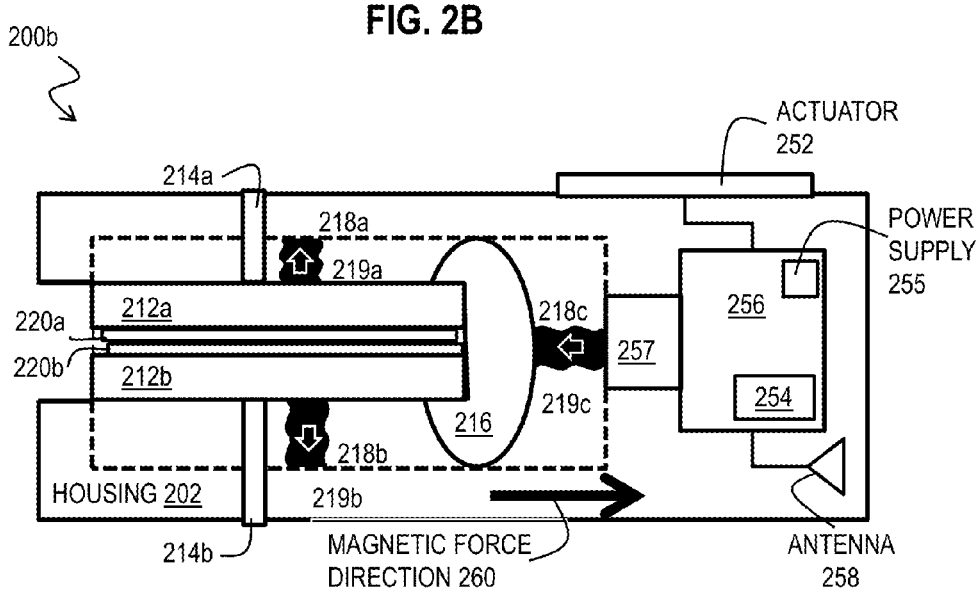

DELAYED RELEASE RESTRAINT SYSTEM

CROSS-REFERENCE TO RELATED APPLICATIONS

This application claims benefit of Provisional Application No. 61/616,595, filed Mar. 28, 2012, the entire contents of which are hereby incorporated by reference as if fully set forth herein, under 35 U.S.C. §119(e).

BACKGROUND OF THE INVENTION

Patient falls are a major problem in healthcare facilities. Patients can be confused from post-operative delirium, medical illness, dementia, or brain injury. These conditions can lead to poor balance, decreased deficit awareness, and impulsivity. Patients will often try to get out of bed without requesting assistance from the medical staff. Even when a patient requests assistance from the medical staff, their delayed response time has been identified as a major cause of patients getting out of bed unassisted.

One way to prevent these injuries is to restrain the patient. Currently, there are two general classes of restraints available. The first class secures the person, but the person can essentially release himself or herself at will. Example mechanisms in this class include Velcro straps, buckles, or seat belts. The second class of restraints is lockable which prevents the person from releasing himself or herself. Generally, in practice, all lockable belts use a universal key. Universal keys are located throughout the facility so that they are readily accessible in an emergency situation. If the patient in the locked belt wants to get up, the patient must either notify the staff directly or request assistance by pressing a nearby call bell. If the call bell is pressed, the patient is forced to remain in place until a staff member responds. This poses a potential safety hazard to the patient in emergency situations. It can also unreasonably limit their autonomy if the staff fails to attend to them within a reasonable time.

In addition to the safety concerns of the lockable restraints, their use is strictly regulated by state law and hospital accreditation guidelines. Many state laws only allow for the use of restraints if they are absolutely necessary to protect the patient or others from injury and less restrictive alternatives prove inadequate. This can mean that a patient must get out of bed and fall before the patient is placed in lockable restraints.

One method that is employed to further ensure patient safety is to install sensors that will notify medical staff of patient movement. For example, sensors can be installed on a patient bed to notify the medical staff when a patient gets up. These sensors serve a limited role in preventing falls because the staff is not alerted until after the patient has gotten up.

SUMMARY OF THE INVENTION

Techniques are provided for a delayed release restraint apparatus and system that provides one or more advantages over the previously available restraint systems. In various embodiments, the system may also serve as both a fall prevention system and a highly advanced call bell system.

In a first set of embodiments, a restraint system includes a restraining strap, a latch and delayed release apparatus. The restraining strap is configured to bind a subject to a support structure. The latch is configured to removably engage at least one of two ends of the restraining strap. The delayed release apparatus includes a first module configured to cause the latch to open, an actuator, and a second module. The second module is configured to cause the first module to open the latch in response to operation of the actuator after a delay of time past the operation of the actuator. The delayed release apparatus is arranged so that the subject can operate the actuator.

In a second set of embodiments, a delayed release apparatus includes a first module, an actuator and a second module. The first module is configured to cause a closed latch to open. The second module is configured to cause the first module to open the latch in response to operation of the actuator after a delay of time past the operation of the actuator.

In a third set of embodiments, a method includes determining that a first signal is received from an actuator, wherein the first signal indicates a request for release from a restraint secured by a latch. The method further includes determining a release time at a delay time after the signal is received, in response to determining that the signal is received. The method still further includes causing the latch to open at the release time. A variation of the third set of embodiments further includes sending a second signal to a remote control panel, wherein the second signal indicates that the first signal has been received. Another variation of the third set of embodiments includes determining whether a third signal is received from the remote control panel, wherein the third signal indicates that the latch can be opened regardless of the release time; and in response to receiving the third signal, causing the latch to open regardless of the release time. Still another variation of the third set of embodiments includes determining whether a second signal is received from an emergency system, wherein the second signal indicates that there is a current evacuation emergency; and in response to receiving the second signal, causing the latch to open regardless of the release time. Yet another variation of the third set of embodiments includes sending a second signal that indicates a request for approval for releasing the latch in response to the local secure release; determining whether a third signal is received, wherein the third signal indicates approval for releasing the latch in response to the local secure release; and causing the latch to open regardless of the release time only in response to determining that the third signal has been received.

In other sets of embodiments, an apparatus or computer-readable medium is configured to perform one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings, in which like reference numerals refer to similar elements, and in which:

FIG. 1C is a block diagram that illustrates an example delayed release restraint system, according to one embodiment;

FIG. 2A and FIG. 2B are block diagrams that illustrate a latch and delayed release apparatus in an open and closed configuration, respectively, according to one embodiment;

DETAILED DESCRIPTION

A method, apparatus and system are described for a delayed release restraint. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of a patient restraint system. However, it should be understood that that this restraint system may be used in a wide range of applications requiring a variable delayed release restraint system. These may include for example, subjects which are prison inmates or livestock. Also, many embodiments are described which exclusively use electronic components; but, in other embodiments, mechanical, chemical, optical or other components are used, in whole or in part, or in any combination. One having ordinary skill in the art would recognize minor changes that would be necessary to adapt the system for different uses. These modifications should be considered part of the invention because they do not deviate from its overall spirit.

Figure 1A:
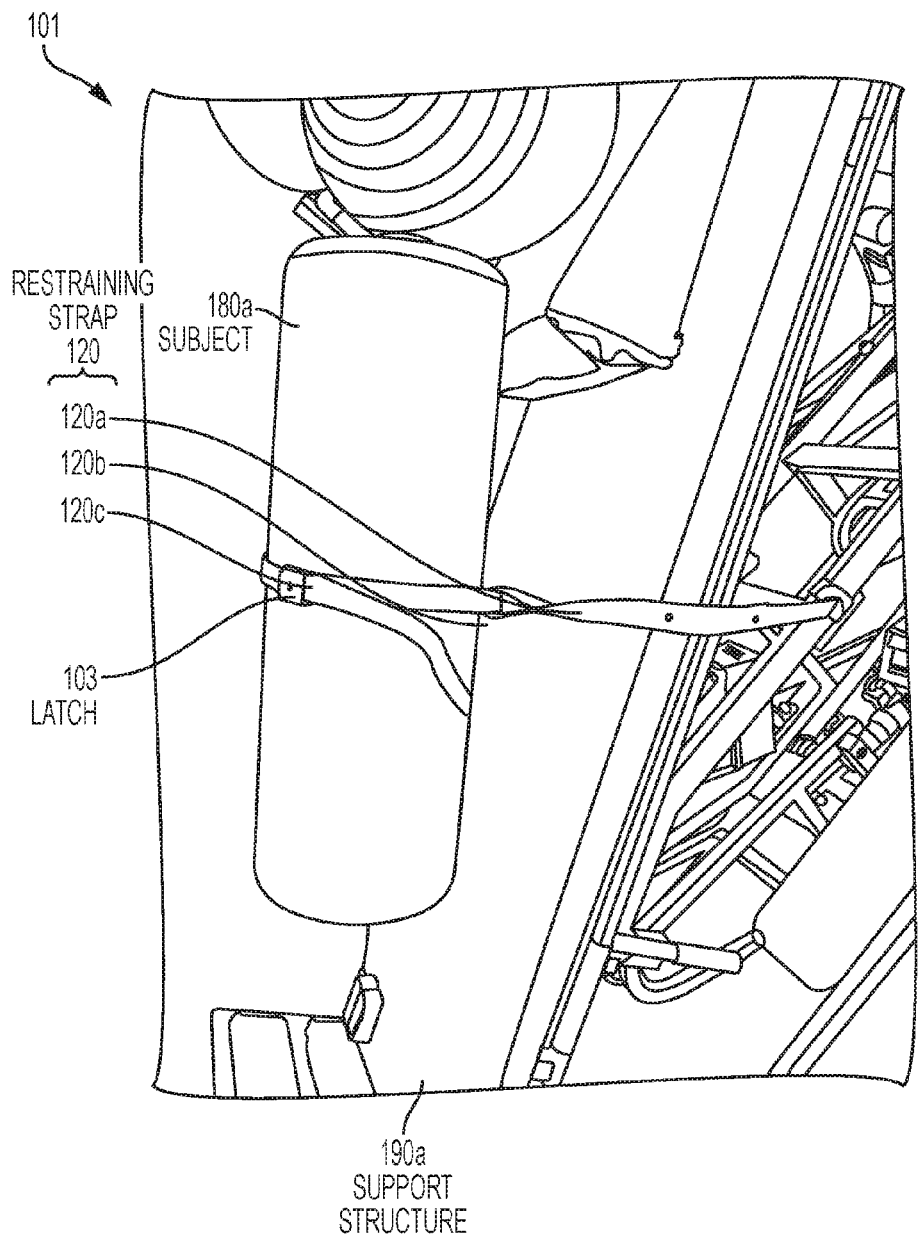
FIG. 1A through FIG. 1B are photographs that illustrate an example restraint system in current use.
Figure 1B:
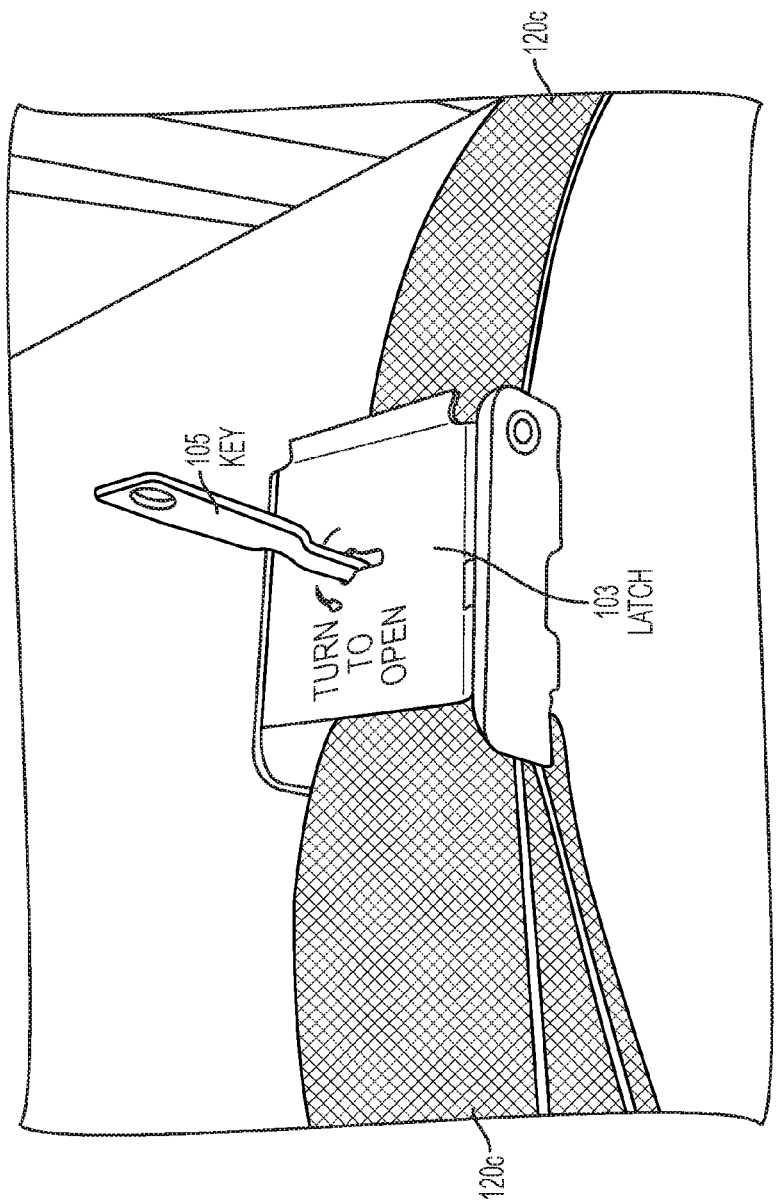

FIG. 1A through FIG. 1B are photographs that illustrate an example restraint system 101 in current use, such as the Swedish Belt from Posey Company of Arcadia, Calif. FIG. 1A depicts the example belt in operation with a surrogate subject 180a. A bolster as a surrogate subject 180a is secured to a subject support structure 190a, such as an articulating table. The belt comprises three webbed nylon straps 120a, 120b, 120c, collectively referenced hereinafter as restraint straps 120. Two straps 120a and 120b have looped proximal ends and are each secured to the support structure 190a by hooks or buckles at the distal ends out of reach of the subject. The third strap 120c passes through the looped proximal ends of the other two straps, passes as a belt around the subject 180a, and the two ends are attached at an arbitrary position using latch 103. The latch 103 is locked so that it cannot be opened by the subject, but can be opened by a staff member. The belt provides the subject with great freedom of movement to rotate around the support and sit or lie flat or take any intervening position, but prevents the subject from moving off the support structure.

FIG. 1B depicts a close up of the latch 103 being secured by a removable key 105. When the key 105 is removed, the subject is powerless to remove the restraint system. The subject must call for staff support to be released.

In consideration of the foregoing, the currently available restraints can prove to be either insufficient or too restrictive. There is no restraining system that balances each individual patient's safety to that patient's right to be autonomous. Further, there is no lockable restraint system that will automatically release in emergency situations. Accordingly, there is a need for a patient restraint system that protects patients from getting up unattended, yet automatically releases the patients if the medical staff fails to attend to them in a timely manner, or in an emergency situation.

FIG. 1C is a block diagram that illustrates an example delayed release restraint system 100, according to one embodiment. A subject 180b and support structure 190b are depicted to illustrate operation of the system 100, but are not part of the restraint system 100. The system 100 includes a restraining strap 122, a latch 110, and a delayed release apparatus 150 with actuator 152 to activate an automatic latch opening module within the apparatus 150. The apparatus 150 also includes opening logic 154a, which is a mechanical or electrical or programmed multipurpose processor (as described below with reference to FIG. 6) configured to cause the apparatus to open the latch after a delay, e.g., after a delay of about 1 minute to about 5 minutes, selected so that a staff member has time to notice and arrive to assist the subject. The actuator 152 is disposed so that the subject 180b can activate the actuator 152. Thus, the restraint system includes a restraining strap configured to bind a subject to a support structure, a latch configured to removably engage at least one of two ends of the restraining strap, and a delayed release apparatus. The delayed release apparatus includes a first module configured to cause the latch to open, an actuator, and a second module configured to cause the first module to open the latch in response to operation of the actuator after a delay of time past the operation of the actuator.

In the illustrated embodiment, the actuator 152 is separate from the rest of the delayed release apparatus 150; but, in some embodiments, the actuator is physically connected to or part of the delayed release apparatus. In the illustrated embodiment, the actuator 152 is in communication with the apparatus 150 though one or more network links, such as network links 140a, 140b and 140c, collectively referenced hereinafter as network links 140. In various embodiments, the network links are hardwired links, such as twisted pair wire or coaxial or fiber optic cable, or are wireless links, or some combination, and include one or more network components such as network interface cards, hubs, bridges and routers on a local area network or wide area network or the public internet.

In the illustrated embodiment, the system 100 also includes a control panel 130 connected to the delayed release apparatus. The control panel 130 is used to remotely control one or more delayed release apparati for corresponding subjects in corresponding locations (e.g., beds, cells, pens) in a facility, such as a farm, clinic, hospital or prison. The control panel 130 is in communication with the one or more delayed release apparati through one or more network links 140. In the illustrated embodiment, some or all of the opening logic, such as opening logic 154b, is included in the control panel 130. In some embodiments, all of the opening logic is in the apparatus 150 and opening logic 154b is omitted. In some embodiments, the control panel is a standalone device. In the illustrated embodiment, the control panel 130 is a program operating on a computer system 160, such as the computer system described in more detail below with reference to FIG. 5.

In some embodiments, an emergency system 170 is connected to the delayed release apparatus 150, either directly through one or more network links 140, or indirectly through the control panel 130, as illustrated in FIG. 1C.

Although processes, equipment, and data structures are depicted in FIG. 1C as integral blocks in a particular arrangement for purposes of illustration, in other embodiments one or more processes or modules or data structures, or portions thereof, are arranged in a different manner, on the same or different hosts, in one or more databases, or are omitted, or one or more different processes or data structures are included on the same or different hosts. System 100 may optionally be configured to be linked to one or more external devices. In various embodiments, such devices may include, for example, a pager, beeper, cell phone, personal digital assistant, tablet, desktop computer, or laptop computer. The applications that are configured for each device enable the medical staff to monitor and perform part or all of the functions of the control panel 130. One having ordinary skill in the art would understand from the teachings provided herein how to configure each device.

System 100 offers solutions that do not invoke the restrictions imposed on other systems, such as system 101, which do not provide for patient autonomy. The delayed release apparatus 150 is a safety device that, although restrictive in nature, allows a patient to release themselves, thus maintaining patient autonomy. The system 100 also serves as an alarm device that, in some embodiments described in more detail below, communicates to hospital personnel that a patient is releasing the restraint. Unlike other alarm or bed sensors on the market, the delay feature of the apparatus 150 gives hospital personnel time to get to a patient's bed side to assist and prevent a potential fall.

Any latch that can be automatically opened by mechanical or electronic or chemical or other means may be used as latch 110 in system 100. FIG. 2A and FIG. 2B are block diagrams that illustrate a latch 210 and delayed release apparatus 250 in an open and closed configuration 200a and 200b, respectively, according to one embodiment. In this embodiment a housing 202 encloses both a latch 210 that is a particular embodiment of latch 110, and delayed release apparatus 250 that is a particular embodiment of apparatus 150.

In open configuration 200a, plates 212a and 212b, collectively referenced hereinafter as plates 212, are pulled apart by springs 218a and 218b, respectively, biased in directions given by arrows indicating spring bias 219a and 219b, respectively. This provides room for one, two or more portions of one or more restraining straps to be inserted into housing 202 between plates 212. In the illustrated embodiment, two portions 220a and 220b of one or two restraining straps are inserted between the plates 212. A C-shape clamp 216 is pushed to the side against the bias 219c of spring 218c by the plates 212 in open configuration 200a. Knobs 214a and 214b (collectively referenced as knobs 214, hereinafter) connected to plates 212a and 212b, respectively, protrude through housing 202 in open configuration 200a. The plates 212, knobs 214, clamp 216, springs 218a, 218b, 218c (collectively referenced hereinafter as springs 218) with biases 219a, 219b, 219c, respectively (collectively referenced hereinafter as spring biases 219) in housing 202 constitute latch 210. In the illustrated embodiment, the clamp 216 is of a metal, such as steel, that responds to a magnetic field.

Adjacent to latch 210, in housing 202, is the delayed release apparatus 250, which includes actuator 252, electromagnet 257 as a latch opening module, and module 256 as a second module to cause the latch opening module to open the latch 210, as described in more detail below.

In the illustrated embodiment, the actuator 252 is accessible outside housing 202, and is electrically connected to module 256, so that a signal is sent to the module 256 when the actuator is activated, such as by touch of a subject or other operator. Any actuator may be used as actuator 252, such as a physical button, a lever, a touch screen, a temperature sensor, a light sensor, or a personal biological identifier, among others, alone or in combination.

The module 256 includes a power supply 255 and opening logic 254, and is connected to an antenna 258 to transmit or receive electromagnetic signals. In some embodiments with the antenna 258, the module 256 includes an electromagnetic transmitter or receive or transceiver. The power supply is any means to power the apparatus, such as an electrical power supply cord, a chemical electrical battery, or mechanical power, such as stored in a wound spring. The opening logic 254 is a particular embodiment of the opening logic 154a or 154b depicted in FIG. 1C, or some combination, and uses one or more of the circuit schematics described below with reference to FIG. 3 to performs one or more of the functions described in more detail below with reference to FIG. 4.

An operator, such as the subject or a staff member of the facility where the subject is restrained, operates the latch to engage portions of one or more restraining straps in the closed configuration 200b, depicted in FIG. 2B. For example, the operator depresses the knobs 214 toward the housing 202, thus moving the plates 212 together against the bias 219a and 219b of springs 218a and 218b, respectively. This also forces the plates against the straps 220, until the spring 218c biased in the direction given by spring bias 219c forces the clamp 216 to engage the plates 212. In this configuration, the plates 212 remain pressed against the straps 220 with sufficient force to keep the straps 220 from sliding; and, the subject is prevented from moving beyond the orbit allowed by the straps 220.

When the opening logic 254 determines that it is time to open the latch 210, either based on activation of the actuator 252 followed by a delay time, or due to other circumstances described in more detail below, then the module 256 powers the electromagnet 257. When powered, the electromagnet 257 applies a magnetic force in the direction 260 to the clamp 216. This pulls the clamp 216 against the spring bias 219c of spring 218c, and away from the plates 212. The plates 212 are then allowed to move to the open configuration 200a in response to springs 218a and 218b pulling in direction given by spring biases 219a and 219b, respectively. This removes the pressure on the straps, which can then be released from the housing. Once the straps are released, the subject is free to escape the orbit of the straps.

Figure 2C:
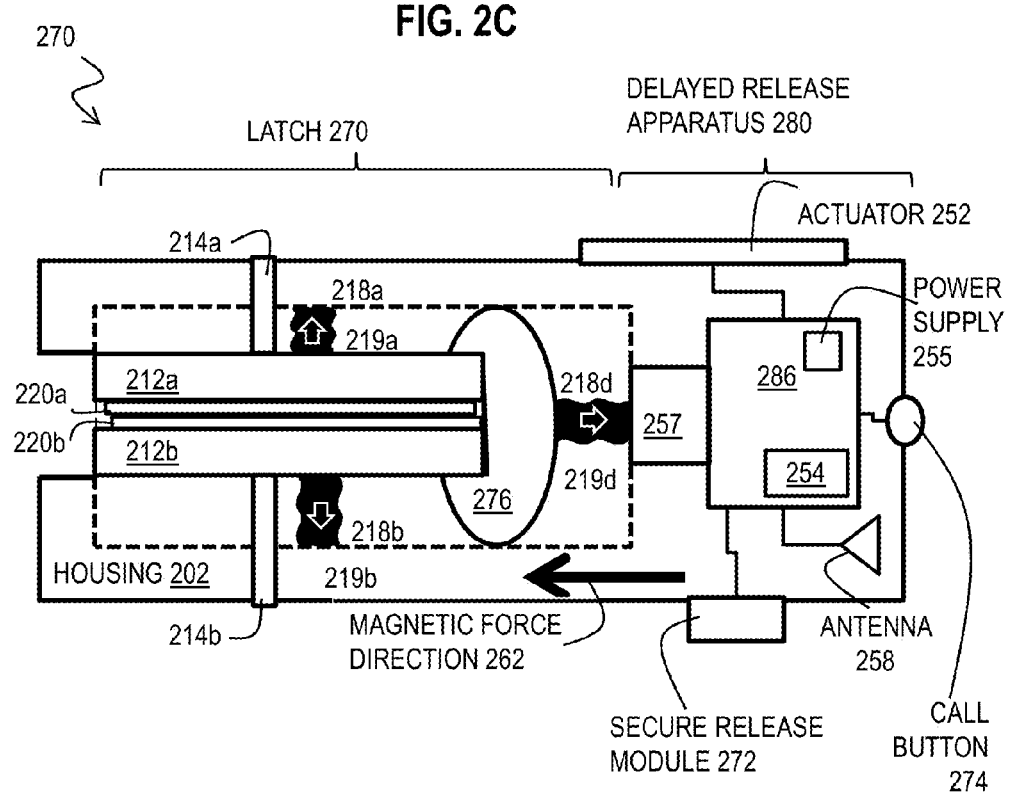
FIG. 2C is a block diagram that illustrates a latch and delayed release apparatus in an closed configuration, according to another embodiment.

In the configuration of FIG. 2B, the straps remain captured if power supply 255 fails (e.g., due to dead batteries or lost power at an electrical outlet feeding power to the apparatus through a power cord). FIG. 2C is a block diagram that illustrates a latch 270 and delayed release apparatus 280 in a closed configuration, according to another embodiment.

In this embodiment, the latch opens if power is lost. The components are the same as in FIGS. 2A and 2B except for a magnetic clamp 276 instead of clamp 216 and different spring 218*d* with a reversed bias 219*d* in lieu of spring 218*c* with bias 219*c*. In the illustrated embodiment, the module 286 also replaces the module 256 to account for the different ways to operate the electromagnet 257. In this embodiment, the electromagnet 257 is on while the plates 212 are engaged by clamp 276. Magnetic clamp 276 has the same magnetic polarity adjacent to the electromagnet 257 as that face of the electromagnetic, setting up a repulsive force in direction 262, which keeps the clamp 276 engaged with plates 212 against the bias 219*d* of spring 218*d*. When the power fails, there is no magnetic force in direction 262; and spring 218 pulls clamp 276 away from plates 212, releasing plates 212 to an open configuration analogous to FIG. 2A, in response to springs 218*a* and 218*b*, respectively.

In the embodiments depicted in FIG. 2A through FIG. 2C, two portions of one or two restraining straps 220 are removably pressed into place between plates 212. In other embodiments, three or more portions of one, two, three or more restraining straps are pressed into place between the two plates, provided there is sufficient friction to prevent easy extraction of a middle strap portion. In other embodiments, one portion of one strap is fixed to the housing 202, and only one portion of the same or different strap is pressed between plates. In some embodiments, one plate is fixed in housing 202 and only the other plate is moveable to be removably engaged by clamp 216 or magnetized clamp 276.

In various embodiments, a delayed release apparatus, such as delayed release apparatus 280, includes a secure release module 272, or a call button 274, or both. The secure release module 272 is configured to allow a staff member to initiate opening the latch, such as latch 210, at the housing 202 in a secure manner that cannot be mimicked by the subject, e.g., with a key or key card. Various methods to configure the secure release module 272 are described in more detail below. The call button 274 is configured to allow an operator, such as the subject or a staff member or family member in the vicinity of the subject to initiate a call to, or conversation with, staff members at a remote location, such as at control panel 130. In some embodiments that include the call button 274, the call button 274 is connected to the module 286 which is configured with a speaker and microphone to facilitate verbal communications.

Figure 2D:
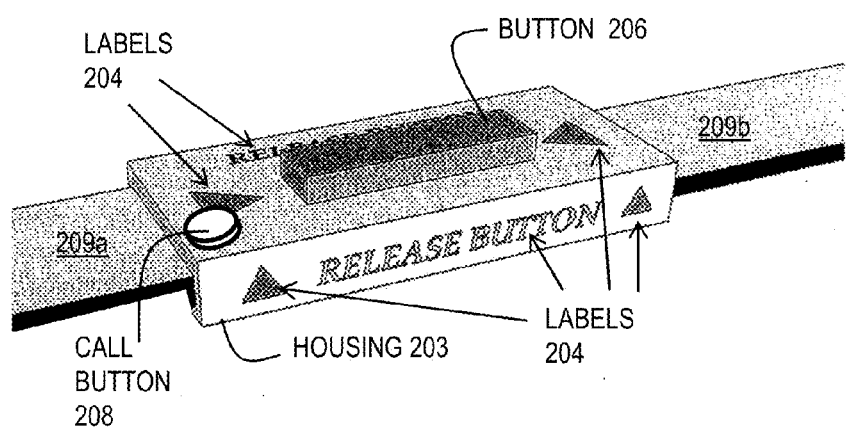
FIG. 2D is a block diagram that illustrates a housing and actuator, according to an embodiment.

FIG. 2D is a block diagram that illustrates a housing and actuator, according to an embodiment. The embodiment is illustrated in a closed configuration of FIG. 2B or FIG. 2C with a button 206, as actuator 252, accessible outside housing 203, such as housing 202, and with straps 209*a* and 209*b*, such as straps 220*a* and 220*b*, compressed in place. The housing 203 includes multiple labels 204 that indicate the actuator is a button 206 to be pressed to release the straps. In the illustrated embodiment, a call button 208, such as call button 274, is also accessible on the surface of the housing 203.

Figure 2E:
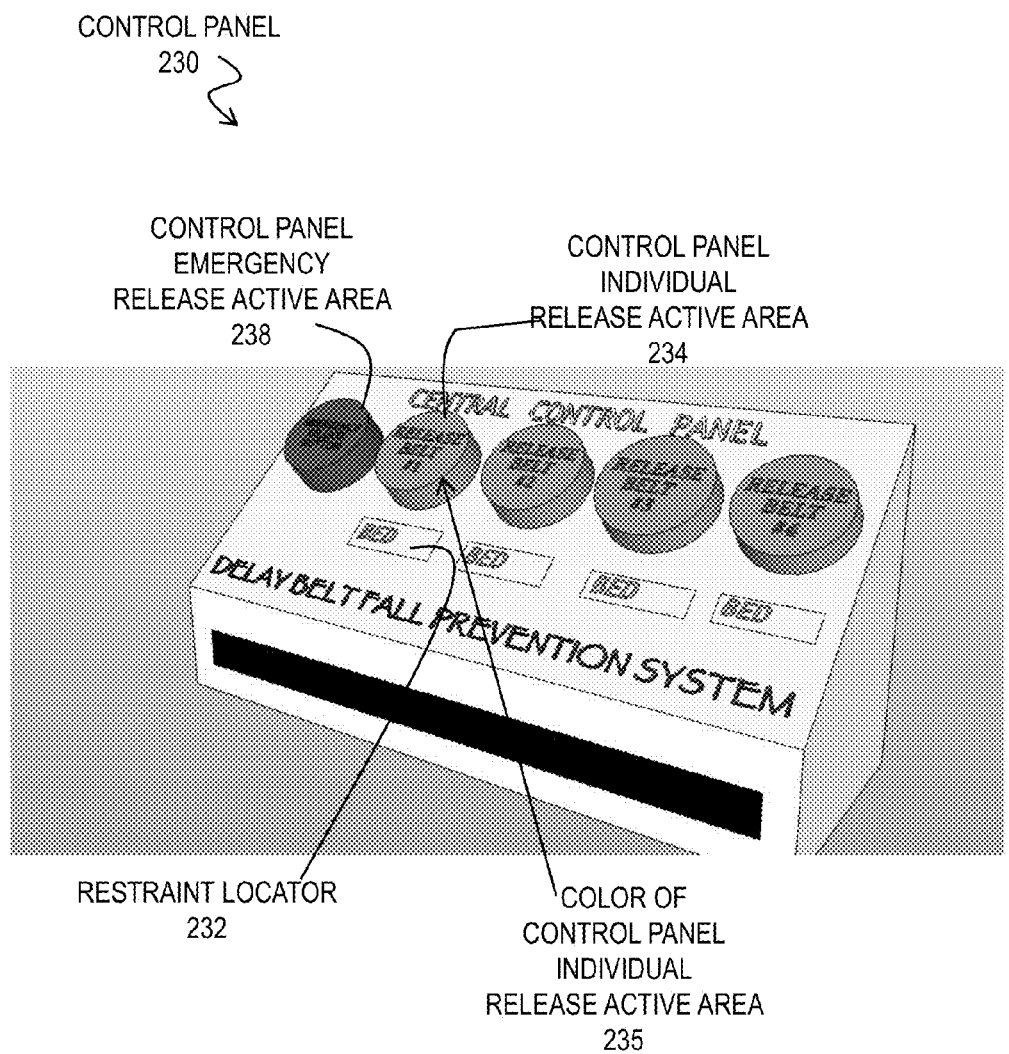
FIG. 2E is a block diagram that illustrates a control panel for a delayed release restraint system, according to an embodiment.

FIG. 2E is a block diagram that illustrates a control panel 230 for a delayed release restraint system, according to an embodiment. In some embodiments, the control panel 230 is a separate device with physical buttons and display fields to indicate labels or colors. In an illustrated embodiment, the control panel 230 is a virtual device evident on a computer screen. Thus, in this embodiment, FIG. 2E is a diagram of a user interface utilized in the processes described herein, and, specifically, illustrates an example screen on a display device of computer system 160. The screen includes one or more active areas that allow a user to input data to operate on data. As is well known, an active area is a portion of a display to which a user can point using a pointing device (such as a cursor and cursor movement device, or a touch screen) to cause an action to be initiated by the device that includes the display. Well known forms of active areas are stand alone buttons, radio buttons, check lists, pull down menus, scrolling lists, and text boxes, among others. Although areas, active areas, windows and tool bars are depicted in FIG. 2E as integral blocks in a particular arrangement on particular screens for purposes of illustration, in other embodiments, one or more screens, windows or active areas, or portions thereof, are arranged in a different order, are of different types, or one or more are omitted, or additional areas are included or the user interface is changed in some combination of ways.

Control panel 230 screen includes individual release active areas 234 for each of one or more delayed release apparatus deployed in a facility. A color 235 of such an active areas 234 indicates the status of the release system 100, e.g., green for locked in place, yellow for requested opening but during delay, orange for request denied, and blue for open, among others. An operator of control panel screen 230 can activate active area 234 to toggle between one of those states.

Below each active area 234 is a restraint locator panel 232 that indicates a location in the facility where the restraint system 100 is in use, such as a bed identifier in a hospital. In some embodiments, the panel 232 is an active area that can be activated to converse with the subject of the restraint or to set one or more delay times for subject initiated or remotely initiated releases. Upon activation, a staff person operating the control panel screen 230 using a speaker and microphone in the housing 202 and the computer system 160 to engage in voice communications with the subject.

A control panel emergency release active area 238 is activated to release all restraints in the facility, e.g., in response to an emergency evacuation. In some embodiments, the active area 238 just indicates the status of emergency, and changes from green when there is no emergency to red when there is an emergency and all restraints are being released.

Another embodiment of the present invention comprises a training system to improve medical staff response time. Here, the control panel is configured to record the events that occur on the system. Reports are then generated from the recorded data which may be displayed at the control panel or transmitted to an external device for review. The medical staff may set the system to generate reports automatically at regular intervals. Other reports may be generated upon request, as needed. The reports may either be retrieved from the display of the control panel or they may be transmitted to an external device. In some embodiments, a notification will automatically be transmitted to an external device if a certain event of interest occurs. For example, if a patient is restrained for an extended period of time which poses a serious danger to that patient's safety, a notification may be emailed to the medical staff supervisor. It is contemplated that such reports will help maintain the level of care and attentiveness of the medical staff.

Figure 3:
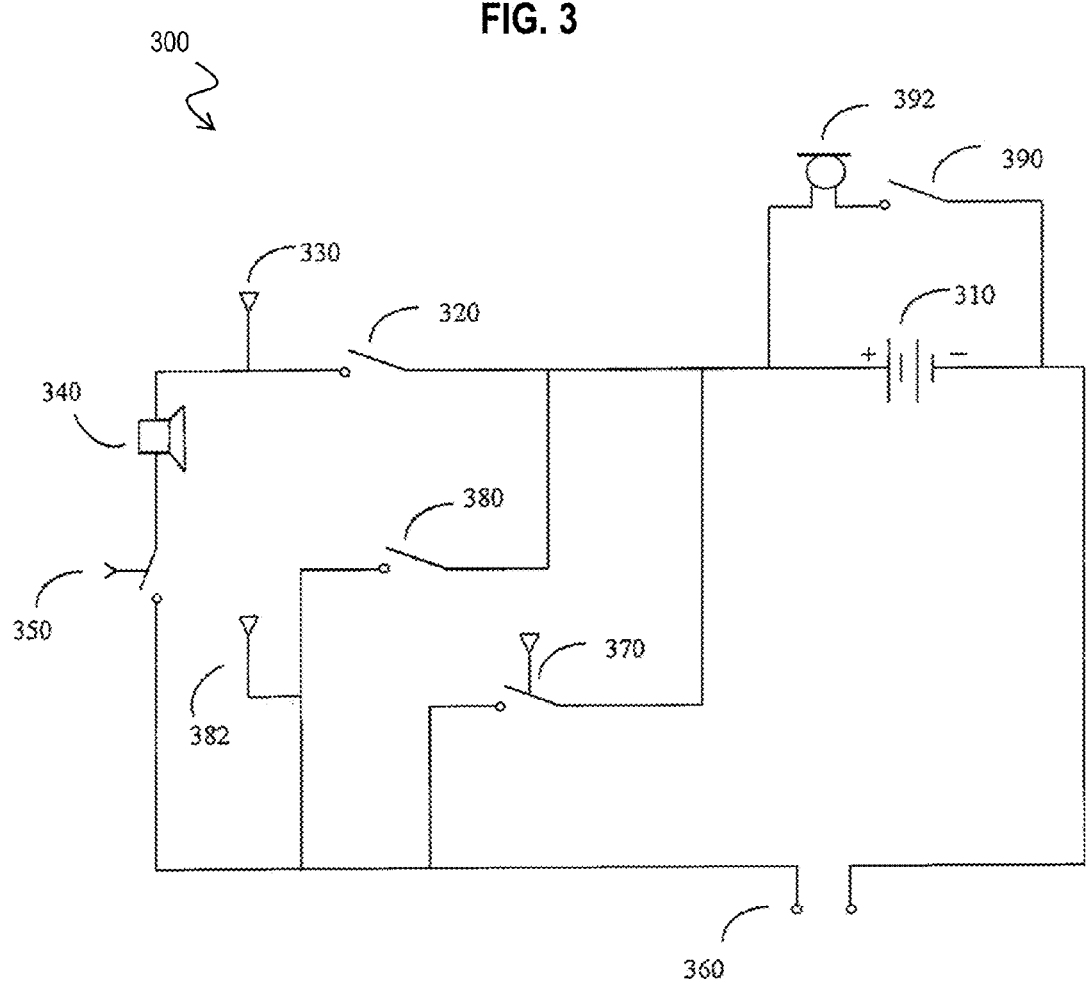
FIG. 3 is a block diagram that illustrates an example electrical schematic of a module of a delayed release apparatus used in the delayed release restraint system, according to another embodiment.

FIG. 3 is a block diagram that illustrates an example electrical schematic of a module 300 of a delayed release apparatus used in the delayed release restraint system, according to another embodiment. In the depicted embodiment, the module 300 is powered with a battery 310. In other embodiments, the module 300 is powered by connecting a cable, not shown, to an electrical outlet. If the patient clicks the release button on the housing, the contact 320 is closed and a signal is transmitted to the central control system 130. In the depicted embodiment, the signal is transmitted wirelessly through transmitter 330. In other embodiments, the module 300 may be hardwired to the central control system which provides the means for which the signal is transmitted. Module 300 may further comprise a speaker 340 which delivers an automated message to inform the patient that the medical staff has been notified of the patient release request and that the latch will release in the set amount of time. In other embodiments, the speaker 340 is a standalone part of the system which is triggered by the wireless transmitter 330. Next, a delay switch 350 is contacted. The delay may be prefixed to a set time or it may be adjusted to the desired time by the medical staff. Once the necessary time elapses, the delay switch contact closes and the latch is released by powering opening module at contacts 360, e.g., by powering (or powering down) electromagnet 257 at contacts 360. In some embodiments, the latch is released remotely from the central control panel. Here, the module 300 contains a receiver connected to a contact 370. The receiver may be wireless or the module 300 may be hardwired into the central control panel. When the signal is received by the module 300 to release the latch, the contact closes and latch is released. The system may be programmed for the latch to be released immediately upon remote release, or have a delayed release.

Module 300 further comprises a manual switch 380. Manual switch 380 provides the medical staff with the ability to unlock the latch at the bedside. In some embodiments, the medical staff will have a magnetic device, such as a magnetic keycard that can be put in close proximity to the module 300 to release the latch. In other embodiments, the manual switch will not be incorporated into the device's electrical system. Instead, the latch is released with a standard key or by a combination code.

Some embodiments having an electronic manual switch 380 include approval at the control panel before the latch is released. When the manual switch is activated, a request is made through transmitter 382 to the control panel. The latch remains closed until approval is granted. In other embodiments, approval is not included and the latch is released immediately. Module 300 may optionally further comprise other elements. For example, in some embodiments, the status of the latch and delayed release apparatus is continuously transmitted to the central control panel. Status measurements may include a battery life indicator and whether or not the latch is locked.

In some embodiments, more than one module 300 is used to restrain a patient. In some of these embodiments, each delayed release apparatus is wired to the other or linked wirelessly so that activation of a mechanism on one apparatus automatically causes the same activation in the other apparatus.

Module 300 in various embodiments is wired to fail open, closed, or as is. If wired to fail open, module 300 automatically open if module 300 loses power or if it loses contact with the control panel. It is contemplated that fail open is an advantageous setting, erring to the side of increased subject autonomy. However, in some embodiments, module 300 may also fail shut, or remain in its current position if the latch loses power or contact with the central control panel.

In some embodiments, module 300 further comprise a microphone to allow for the patient to communicate with the medical staff at the control panel. In the depicted embodiment, the patient presses a communication button 390 on the housing. When button 390 is pressed, the patient's voice is received by microphone 392 and transmitted to the control panel. In the depicted embodiment, the patient communicates with the staff at the control panel at any time. In other embodiments, button 390 serves as a communication request. In these embodiments, the medical staff accepts the request at the control panel before microphone 392 receives the patient's voice. In some embodiments, speaker 340 is configured to transmit communication from the medical staff at the control panel to the patient. In other embodiments, a separate speaker is added to the system to relay the communication from the control panel. The communication aspect of this invention as depicted in element 390, 392, and 340 may be part of the delayed release apparatus. Alternatively, it may be a separate device that is integrated into the call bell system.

Figure 4:
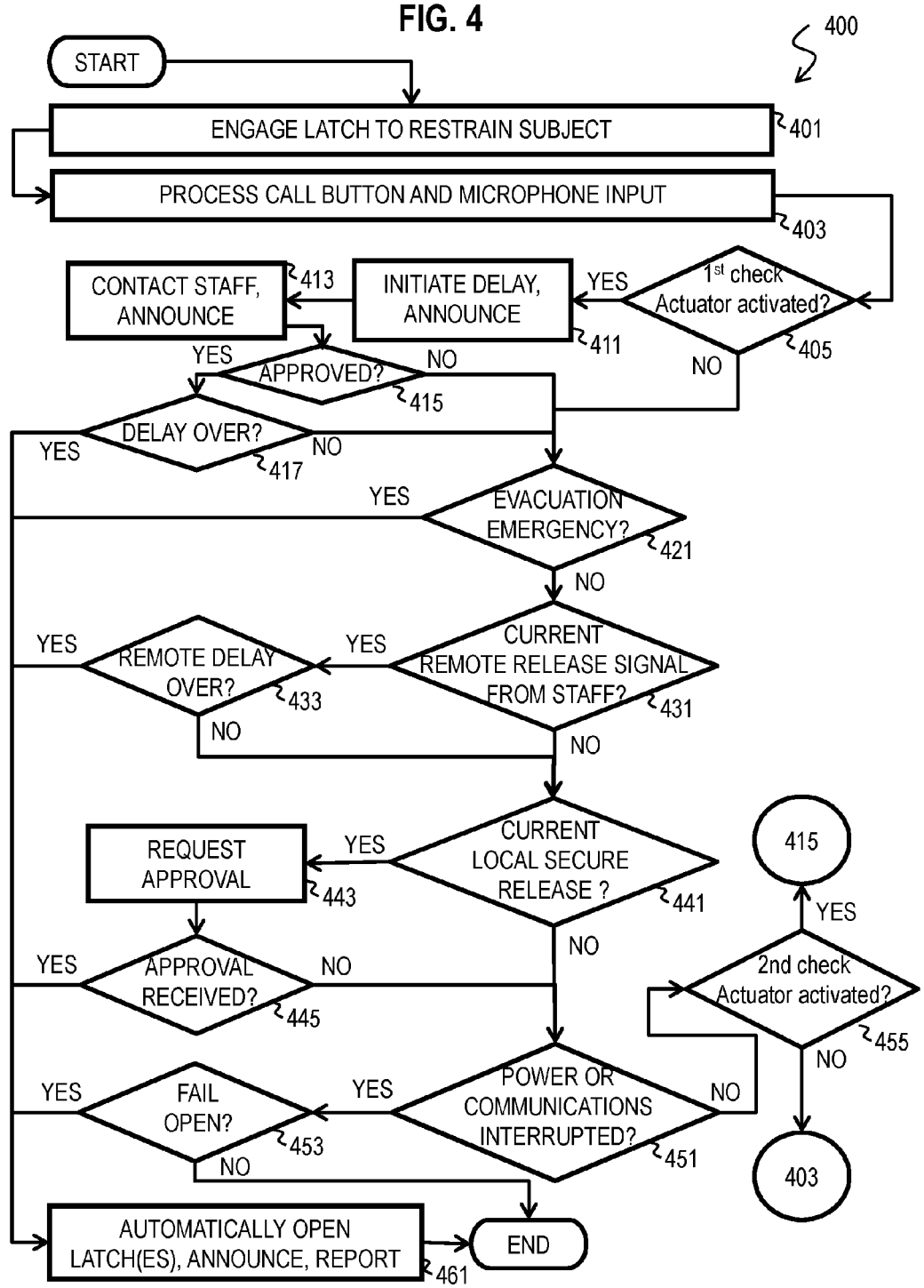
FIG. 4 is a flow chart that illustrates an example method for providing a delayed release restraint system, according to an embodiment.

FIG. 4 is a flow chart that illustrates an example method 400 for providing a delayed release restraint system, according to an embodiment. Although steps are depicted in FIG. 4 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. The steps of FIG. 4 are executed by a module of the delayed release apparatus 150 according to the opening logic 154 on the module, or by control panel 130, or by some combination.

In step 401, the latch is engaged to restrain a subject. For example, one or more straps of a restraint system are placed between plates 212 of the device in FIG. 2A or FIG. 2C and knobs 214 are pressed toward the housing 202 by a staff member, such as a medical professional, until clamp 216 engages the plates in the configuration 200b of FIG. 2B or FIG. 2C. The latch remains so engaged unless one of the conditions for releasing the latch is satisfied, as described in the following steps.

In step 403, the system 100 is used as a call button so the subject can call or converse with the staff or vice versa, e.g., using the microphone 392 and speaker 340 depicted in FIG. 3 for the module 256 or module 286 of FIG. 2A through FIG. 2C. In such embodiments, the housing includes a call button 274 in housing 202, as depicted in FIG. 2C, which is depressed to speak with a staff member at the control panel 130. In some embodiments, the actuator 252 is a call button used to request a release verbally; and, a separate call button 274 is omitted.

In step 405, it is determined whether an operator, such as the subject or a staff member, has activated the actuator, such as actuator 252. In the preferred embodiment, a patient request is made by pressing a button on the latch. In other embodiments the patient request mechanism is a separate device. For example, the mechanism is a separate call bell or it a voice activated mechanism, in various embodiments. If not, control passes to step 421 and following steps, described below, to open only upon the satisfaction of at least one of one or more other conditions.

If the actuator has been activated, control passes to step 411 to initiate the mechanism to start the delay time. In some embodiments, step 411 includes an announcement that the delayed release has been initiated and the latch will be opened in a stated amount of time, e.g., about one to five minutes. In various embodiments, the announcement is a recorded voice, an automated voice, a textual display, or a live voice from a staff member.

In step 413, the staff is contacted, e.g., by sending a signal to the control panel 130. In some embodiments, step 413 includes an announcement for the benefit of the subject that the staff has been contacted and will appear in due course.

The signal transmitted in step 413 to the control panel indicates a request has been made. In some embodiments, the patient request indicator on the control panel varies depending on the settings. Indicators include, for example, a color change, a flashing light, a single or repetitive noise, or an announcement. In some examples, the medical staff is notified of the release in a countdown fashion at preset intervals. For example, if the patient in Bed 2 who has a delayed release time of more than one minute, makes a request, the control panel makes an announcement in one minute intervals that "Bed 2 will release in X minutes" where X is the amount of time until the latch is released. In various setting or embodiments, the countdown interval may be any desired time amount, including, but not limited to every minute, every thirty seconds, every fifteen seconds, every ten seconds, every five seconds, or every one second, or some combination. In some settings, the interval of the countdown announcement changes as the release time approaches. In one example, the countdown starts at one minute intervals, but once the timer is below one minute, announcements occur at thirty seconds and every ten seconds thereafter. The indication mode also changes, in some embodiments, as the countdown approaches the release time. For example, when the request is first made a less disruptive indicator is triggered such as a single beep. However, as the time to release approaches, the number of beeps increases or gets louder.

Another example is provided where the delay mechanism includes the ability to program a variable delay time. For instance, for a patient who is only mildly confused staff might set the time for delay to be a minute. For a more impaired patient the staff might want 5 minutes. This may be predicated on staffing as well. So for a nurse to patient ratio of 1:8 the staff might set it at 5 minutes; whereas for a ratio of 1:3 the staff might set the delay at 3 minutes. For a more high level patient, the staff might set the delay at zero. In this case the staff is alerted that the patient is out of bed but there is no urgency to get there. Thus, the release delay can be programmed according to circumstances.

In step 415, it is determined whether approval for the delayed release has been obtained, for example by an approval signal from the control panel 130 initiated by a staff member. In some embodiments, approval is not included and step 415 is omitted, and control passes directly to step 417. In embodiments that include approval by staff, the control panel 130 provides the medical staff with the ability to deny the request or extend the delayed release time. In these example embodiments, if a request is denied, the latch is not unlocked at the pre-set time. Instead, the system status reverts to that of a non-activated actuator; and, the latch remains locked unless one of the other conditions is satisfied. Control passes to step 421. In some embodiments, if a request is denied, another request cannot be transmitted in step 413 until a pre-set amount of time has passed, and the announcement made during step 413 so states. If the medical staff does not override a patient request, then control passes to step 417.

In step 417, it is determined if the delay time is over. If not, control passes to step 421 and following steps, described below to open only upon satisfaction of one or more other conditions. If the delay time is over, at the pre-set time interval, control passes to step 461.

In step 461, the latch is automatically opened by the opening module, such as electromagnet 257, of the apparatus 150. When the latch is opened, a module of apparatus 150, e.g., module 256, signals the control panel of the open status. Once the open signal is received by the control panel 130, the patient request indicator at the control panel stops and the open status is indicated.

In some embodiments, an emergency can cause a release of the latch. Such embodiments include step 421. In other embodiments, step 421 is omitted. In step 421, it is determined whether there is an evacuation emergency. If so, control passes immediately to step 461 to automatically open the latch, as described above. Any method may be used to determine whether there is an evacuation emergency. For example, in some embodiments, the control pane 1301 is connected to a fire alarm or other central or local emergency system. In some embodiments, the system 100 is hardwired or wirelessly integrated with one or more of these emergency systems. In various embodiments, the emergency systems is integrated into the control panel 130, or directly to each individual delayed release apparatus 150, such as via antenna 258 to module 256 of apparatus 250. In certain embodiments, the latch is automatically released if the delayed release apparatus receives a signal from the emergency system or loses contact with it. In other embodiments, the system 100 is configured so that the emergency system signals the delayed release apparatus to automatically lockdown if certain events occur. In the example method 400, the latch remains locked unless a signal is received from the fire alarm or unless the connection is lost to the emergency system. If either occurs, control passes to step 461 described above.

In some embodiments, the staff at a remote site, such as at control panel 130, can request a release of the latch, either immediately or after a specified or predetermined delay. Such embodiments include steps 431 and 433. In other embodiments, steps 431 and 433 are omitted. In step 431, it is determined whether there is a current (unsatisfied) release signal received remotely from a staff member. If not, control passes to step 441 and following to test for other conditions for opening the latch. However, if a remote release signal has been received but not yet satisfied, control passes to step 433. In step 433, it is determined whether the delay for the release based on the remote signal is over. If so, control passes to step 461, described above, to open the latch. If not, control passes to step 441. In some embodiments, no delay is imposed upon the remote release signal; and, step 433 is omitted so control passes directly to step 461. Using steps 431 and 433, the latch is released by manually initiating opening of the latch at the control panel 130. A signal is sent to the delayed release apparatus 150, such as module 256, to unlock the latch. In some embodiments, the control panel allows the medical staff at the control panel 130 to order a delayed release. In other embodiments, the override at the control panel will send a signal to immediately open the latch.

In some embodiments, the staff locally at the site of the restrained subject can request a release of the latch, either immediately or after approval from a remote staff member or a staff member of higher authority. Such a request is distinguished from requests by the subject using any means, such as a key, a key card with a magnetic strip or radio frequency identifier circuit (RFID), a secret code on a keypad, or any other known means, e.g., using the secure release module 272 depicted in FIG. 2C. Such embodiments include steps 441, 443 and 435. In other embodiments, steps 441, 443 and 435 are omitted.

Thus, in these embodiments, the latch is manually opened. In step 441 it is determined whether there is a current local secure release (a local release attempted and not yet satisfied), e.g., using a key card or other device, as described above. In some examples, a manual request at the latch automatically releases the latch; and, steps 443 and 445 are omitted so control passes directly to step 461. In other embodiments, when a manual release is attempted, a signal is sent to the control panel in step 443 with a request to allow the release. It is determined at step 445 whether approval is received from medical staff at the control station 130. If not, the latch remains locked; and control passes to step 451 and following to open the lock only upon satisfaction of another condition. In some embodiments, if the request is not approved at the control panel within a preset amount of time, the request is automatically either denied or allowed, depending on preset settings. If the request is accepted, control passes to step 461 and the latch is unlocked immediately. It is contemplated that steps 443 and 445 are advantageously used if the staff members have different levels of access with their access cards. For example, staff members with higher access will not use steps 443 and 445; but, those with a lower access level are subjected to steps 443 and 445.

In some embodiments, the latch is opened (or, in some embodiments, closed) upon power failure or loss of communication with the remote staff at control panel 130, or both. Such embodiments include steps 451 and 453. In other embodiments, steps 451 and 453 are omitted. In step 451, it is determined whether there is a loss of power or communication with control panel 130. In some embodiments, an outage of an extended time, such as several multiples of the delay time (e.g., about 2 to about 6 multiples of a delay time of about 1 minute to about 6 minutes, for a time in a range of about 2 minutes to about 36 minutes), with multiple attempt to reestablish communication involved before determining that there is a loss of communication.

If it is determined in step 451 that there is a loss of power or loss of communication, then control passes to step 453 to determine whether the latch should be opened (fail open) or closed (fail close) in the event of a power or communication failure. In some embodiments, fail open or fail closed upon a power failure is built into the apparatus. For example, the apparatus of FIG. 2B remains as it is (either open or closed) in the event of a power failure, while the device of FIG. 2C will open a closed latch in the event of a power failure. If the latch is to be open in case of a power or communication loss (fail open), then control passes to step 461, described above. In some embodiments, in the event of a power loss there may be insufficient power to announce or report the opening. In some embodiments, a charged capacitor in the opening apparatus, such as in module 256, can be used to power the opening of the latch and the announcing and reporting even in the event of a loss of battery or outlet power.

Thus, in some embodiments, the latch is automatically opened if the delayed release apparatus loses power; and, in some embodiments, is also released if the signal to the control panel 130 is lost. In some example embodiments, the latch is automatically released when the signal to the control panel is lost. In other examples, the automatic release is delayed for a preset amount of time in order to try and regain the signal to the control panel. If the signal is regained within that time, then the latch will remain locked. When the latch is released, the latch will attempt to signal the control panel of the unlocked status, during step 461.

If none of the included conditions for opening the latch are satisfied, control passes to step 455. In step 455 it is determined whether the apparatus is in the opening requested state (actuator activated state), or not. If so, control passes back to step 415 to determine whether the delay is over. If not, control passes back to step 403 to act as a call button and begin again testing for a conditions to be satisfied for opening the latch, as described above.

Figure 5:
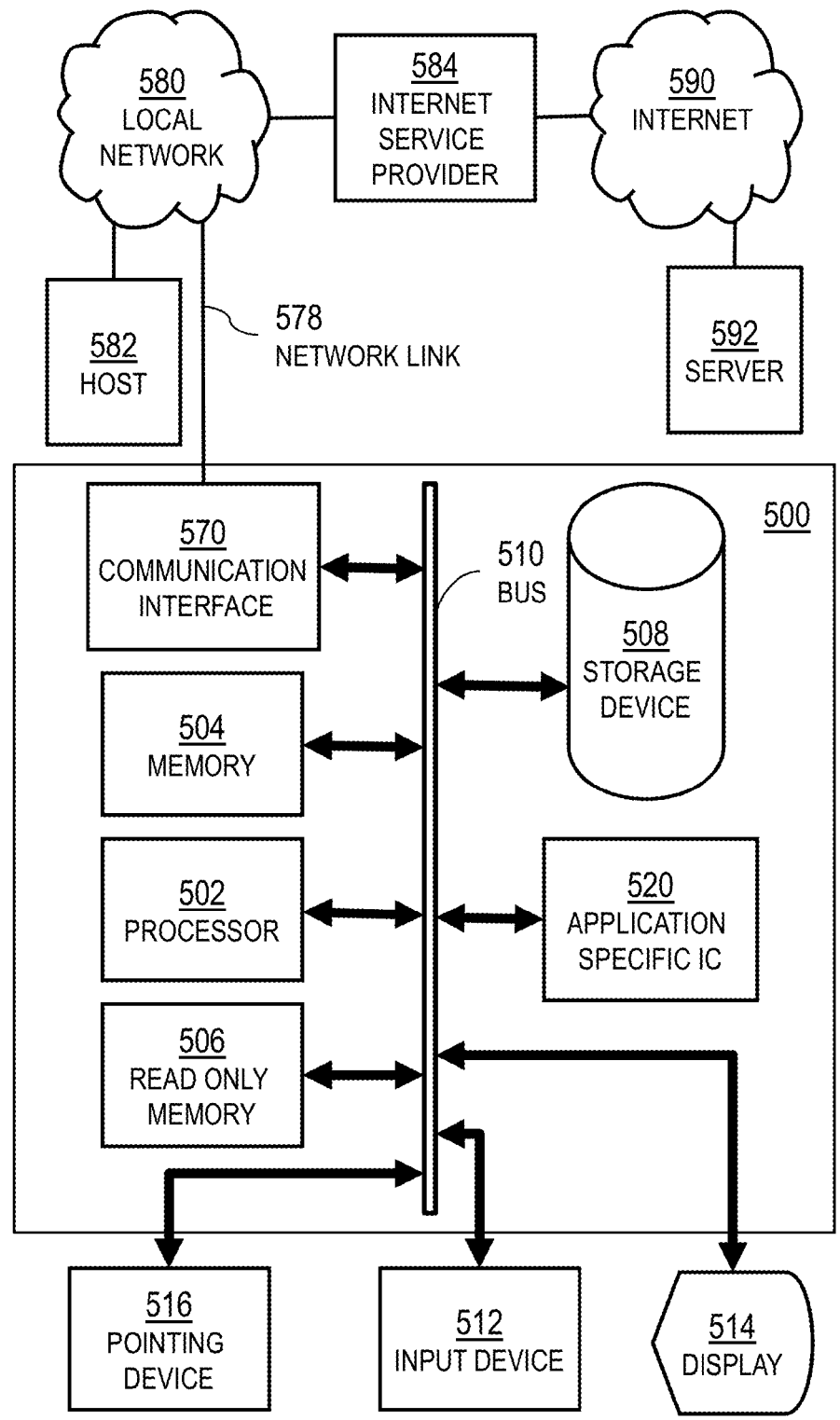
FIG. 5 is a block diagram that illustrates a computer system upon which an embodiment of the invention may be implemented.

FIG. 5 is a block diagram that illustrates a computer system 500 upon which an embodiment of the invention may be implemented. Computer system 500 includes a communication mechanism such as a bus 510 for passing information between other internal and external components of the computer system 500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 500, or a portion thereof, constitutes a means for performing one or more steps of one or more methods described herein.

A sequence of binary digits constitutes digital data that is used to represent a number or code for a character. A bus 510 includes many parallel conductors of information so that information is transferred quickly among devices coupled to the bus 510. One or more processors 502 for processing information are coupled with the bus 510. A processor 502 performs a set of operations on information. The set of operations include bringing information in from the bus 510 and placing information on the bus 510. The set of operations also typically include comparing two or more units of information, shifting positions of units of information, and combining two or more units of information, such as by addition or multiplication. A sequence of operations to be executed by the processor 502 constitutes computer instructions.

Computer system 500 also includes a memory 504 coupled to bus 510. The memory 504, such as a random access memory (RAM) or other dynamic storage device, stores information including computer instructions. Dynamic memory allows information stored therein to be changed by the computer system 500. RAM allows a unit of information stored at a location called a memory address to be stored and retrieved independently of information at neighboring addresses. The memory 504 is also used by the processor 502 to store temporary values during execution of computer instructions. The computer system 500 also includes a read only memory (ROM) 506 or other static storage device coupled to the bus 510 for storing static information, including instructions, that is not changed by the computer system 500. Also coupled to bus 510 is a non-volatile (persistent) storage device 508, such as a magnetic disk or optical disk, for storing information, including instructions, that persists even when the computer system 500 is turned off or otherwise loses power.

Information, including instructions, is provided to the bus 510 for use by the processor from an external input device 512, such as a keyboard containing alphanumeric keys operated by a human user, or a sensor. A sensor detects conditions in its vicinity and transforms those detections into signals compatible with the signals used to represent information in computer system 500. Other external devices coupled to bus 510, used primarily for interacting with humans, include a display device 514, such as a cathode ray tube (CRT) or a liquid crystal display (LCD), for presenting images, and a pointing device 516, such as a mouse or a trackball or cursor direction keys, for controlling a position of a small cursor image presented on the display 514 and issuing commands associated with graphical elements presented on the display 514.

In the illustrated embodiment, special purpose hardware, such as an application specific integrated circuit (IC) 520, is coupled to bus 510. The special purpose hardware is configured to perform operations not performed by processor 502 quickly enough for special purposes. Examples of application specific ICs include graphics accelerator cards for generating images for display 514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 500 also includes one or more instances of a communications interface 570 coupled to bus 510. Communication interface 570 provides a two-way communication coupling to a variety of external devices that operate with their own processors, such as printers, scanners and external disks. In general the coupling is with a network link 578 that is connected to a local network 580 to which a variety of external devices with their own processors are connected. For example, communication interface 570 may be a parallel port or a serial port or a universal serial bus (USB) port on a personal computer. In some embodiments, communications interface 570 is an integrated services digital network (ISDN) card or a digital subscriber line (DSL) card or a telephone modem that provides an information communication connection to a corresponding type of telephone line. In some embodiments, a communication interface 570 is a cable modem that converts signals on bus 510 into signals for a communication connection over a coaxial cable or into optical signals for a communication connection over a fiber optic cable. As another example, communications interface 570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 570 sends and receives electrical, acoustic or electromagnetic signals, including infrared and optical signals, that carry information streams, such as digital data.

The term computer-readable medium is used herein to refer to any medium that participates in providing information to processor 502, including instructions for execution. Such a medium may take many forms, including, but not limited to, non-volatile media, volatile media and transmission media. Non-volatile media include, for example, optical or magnetic disks, such as storage device 508. Volatile media include, for example, dynamic memory 504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 502, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 502, except for carrier waves and other signals.

Logic encoded in one or more tangible media includes one or both of processor instructions on a computer-readable storage media and special purpose hardware, such as ASIC 520.

Network link 578 typically provides information communication through one or more networks to other devices that use or process the information. For example, network link 578 may provide a connection through local network 580 to a host computer 582 or to equipment 584 operated by an Internet Service Provider (ISP). ISP equipment 584 in turn provides data communication services through the public, world-wide packet-switching communication network of networks now commonly referred to as the Internet 590. A computer called a server 592 connected to the Internet provides a service in response to information received over the Internet. For example, server 592 provides information representing video data for presentation at display 514.

The invention is related to the use of computer system 500 for implementing the techniques described herein. According to one embodiment of the invention, those techniques are performed by computer system 500 in response to processor 502 executing one or more sequences of one or more instructions contained in memory 504. Such instructions, also called software and program code, may be read into memory 504 from another computer-readable medium such as storage device 508. Execution of the sequences of instructions contained in memory 504 causes processor 502 to perform the method steps described herein. In alternative embodiments, hardware, such as application specific integrated circuit 520, may be used in place of or in combination with software to implement the invention. Thus, embodiments of the invention are not limited to any specific combination of hardware and software.

The signals transmitted over network link 578 and other networks through communications interface 570, carry information to and from computer system 500. Computer system 500 can send and receive information, including program code, through the networks 580, 590 among others, through network link 578 and communications interface 570. In an example using the Internet 590, a server 592 transmits program code for a particular application, requested by a message sent from computer 500, through Internet 590, ISP equipment 584, local network 580 and communications interface 570. The received code may be executed by processor 502 as it is received, or may be stored in storage device 508 or other non-volatile storage for later execution, or both. In this manner, computer system 500 may obtain application program code in the form of a signal on a carrier wave.

Various forms of computer readable media may be involved in carrying one or more sequence of instructions or data or both to processor 502 for execution. For example, instructions and data may initially be carried on a magnetic disk of a remote computer such as host 582. The remote computer loads the instructions and data into its dynamic memory and sends the instructions and data over a telephone line using a modem. A modem local to the computer system 500 receives the instructions and data on a telephone line and uses an infra-red transmitter to convert the instructions and data to a signal on an infra-red a carrier wave serving as the network link 578. An infrared detector serving as communications interface 570 receives the instructions and data carried in the infrared signal and places information representing the instructions and data onto bus 510. Bus 510 carries the information to memory 504 from which processor 502 retrieves and executes the instructions using some of the data sent with the instructions. The instructions and data received in memory 504 may optionally be stored on storage device 508, either before or after execution by the processor 502.

Figure 6:
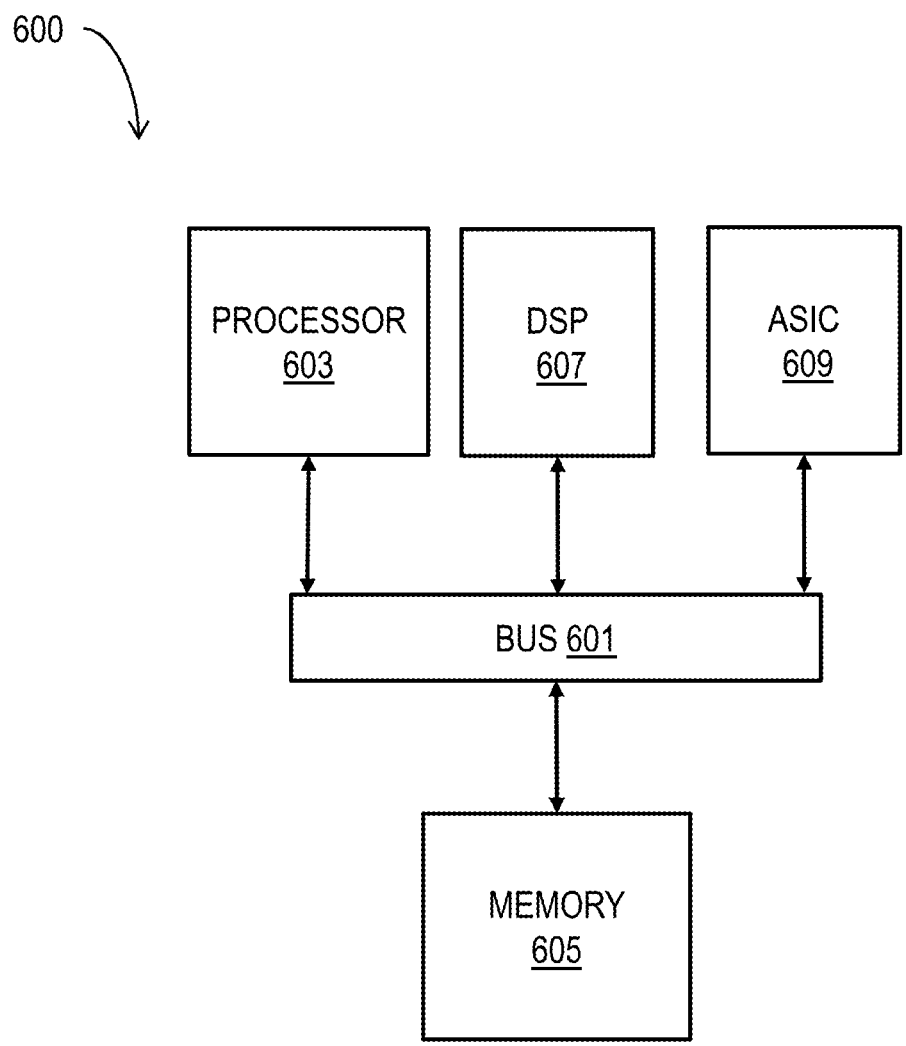
FIG. 6 illustrates a chip set upon which an embodiment of the invention may be implemented.

FIG. 6 illustrates a chip set 600 upon which an embodiment of the invention may be implemented. Chip set 600 is programmed to perform one or more steps of a method described herein and includes, for instance, the processor and memory components described with respect to FIG. 5 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 600, or a portion thereof, constitutes a means for performing one or more steps of a method described herein.

In one embodiment, the chip set 600 includes a communication mechanism such as a bus 601 for passing information among the components of the chip set 600. A processor 603 has connectivity to the bus 601 to execute instructions and process information stored in, for example, a memory 605. The processor 603 may include one or more processing cores with each core configured to perform independently. A multi-core processor enables multiprocessing within a single physical package. Examples of a multi-core processor include two, four, eight, or greater numbers of processing cores. Alternatively or in addition, the processor 603 may include one or more microprocessors configured in tandem via the bus 601 to enable independent execution of instructions, pipelining, and multithreading. The processor 603 may also be accompanied with one or more specialized components to perform certain processing functions and tasks such as one or more digital signal processors (DSP) 607, or one or more application-specific integrated circuits (ASIC) 609. A DSP 607 typically is configured to process real-world signals (e.g., sound) in real time independently of the processor 603. Similarly, an ASIC 609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 603 and accompanying components have connectivity to the memory 605 via the bus 601. The memory 605 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 605 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

What is claimed is:

1. A restraint system comprising:
   a restraining strap configured to bind a subject to a support structure;
   a latch configured to removably engage at least one of two ends of the restraining strap; and
   a delayed release apparatus comprising a first module configured to cause the latch to open;
   an actuator, and
   a second module configured to cause the first module to open the latch in response to operation of the actuator after a delay of time past the operation of the actuator,
   wherein the second module further comprises a communications module and, the second module is further configured to cause the first module to open the latch in response to a signal that indicates the latch is to be released,
   wherein the signal is received from a remote control panel and to cause the first module to open the latch is response to a loss of communication with the remote control panel,
   wherein the delayed release apparatus is arranged so that the subject can operate the actuator.

2. An apparatus comprising:
   a first module configured to cause a closed latch to open;
   an actuator; and
   a second module configured to cause the first module to open the latch in response to operation of the actuator after a delay of time past the operation of the actuator,
   wherein the second module further comprises a communications module and, the second module is further configured to cause the first module to open the latch in response to a signal that indicates the latch is to be released,
   wherein the signal is received from a remote control panel and to cause the first module to open the latch in response to a loss of communication with the remote control panel.

3. The apparatus as recited in claim 2, wherein the second module is further configured to cause the first module to open the latch in response to a signal that indicates emergency evacuation.

4. The apparatus as recited in claim 2, wherein the second module is further configured to cause the first module to open the latch in response to a loss of power.

5. The apparatus as recited in claim 2, wherein:
   the apparatus further comprises a local secure release module; and,
   the second module is further configured to cause the first module to open the latch in response to operation of the local secure release module.

6. A method comprising:
   determining that a first signal is received from an actuator, wherein the first signal indicates a request for release from a restraint secured by a latch;
   in response to determining that the signal is received, determining a release time at a delay time after the signal is received;
   causing the latch to open at the release time;
   causing the latch to open in response to a signal that indicates the latch is to be released,
   wherein the signal is received from a remote control panel; and
   causing the latch to open in response to a loss of communication with the remote control panel.

7. The method as recited in claim 6, further comprising sending a second signal to a remote control panel, wherein the second signal indicates that the first signal has been received.

8. The method as recited in claim 7, wherein causing the latch to open in response to a signal received from a remote control panel further comprises:
   determining whether a third signal is received from the remote control panel, wherein the third signal indicates that the latch can be opened regardless of the release time; and
   in response to receiving the third signal, causing the latch to open regardless of the release time.

9. The method recited in claim 6, further comprising:
   determining whether a second signal is received from an emergency system, wherein the second signal indicates that there is a current evacuation emergency; and
   in response to receiving the second signal, causing the latch to open regardless of the release time.

10. The method as recited in claim 6, further comprising:
   determining whether a local secure release has been initiated; and
   in response to determining that the local secure release has been initiated, causing the latch to open regardless of the release time.

11. The method as recited in claim 10, wherein causing the latch to open regardless of the release time further comprises:
   sending a second signal that indicates a request for approval for releasing the latch in response to the local secure release;
   determining whether a third signal is received, wherein the third signal indicates approval for releasing the latch in response to the local secure release; and
   causing the latch to open regardless of the release time only in response to determining that the third signal has been received.

12. The method as recited in claim 6, further comprising:
   determining whether power is lost; and
   in response to determining that power is lost,
   causing the latch to open regardless of the release time.

13. A non-transitory computer-readable medium carrying one or more sequences of instructions, wherein execution of the one or more sequences of instructions by one or more processors causes an apparatus to perform at least the following:
   determine that a first signal is received from an actuator, wherein the first signal indicates a request for release from a restraint secured by a latch;
   in response to determining that the signal is received, determine a release time at a delay time after the signal is received;
   cause the latch to open at the release time;
   causing the latch to open in response to a signal that indicates the latch is to be released,
   wherein the signal is received from a remote control panel; and
   causing the latch to open in response to a loss of communication with the remote control panel.

* * * * *